United States Patent
Attariwala (10) Patent No.: US 11,636,589 B2
(45) Date of Patent: Apr. 25, 2023

(54) IDENTIFICATION OF CANDIDATE ELEMENTS IN IMAGES FOR DETERMINATION OF DISEASE STATE USING ATLAS ELEMENTS

(71) Applicant: Vigilance Health Imaging Network Inc., Montréal (CA)

(72) Inventor: Rajpaul Attariwala, Vancouver (CA)

(73) Assignee: Vigilance Health Imaging Network Inc., Montréal (CA)

( * ) Notice: Subject to any disclaimer, the term of this patent is extended or adjusted under 35 U.S.C. 154(b) by 208 days.

(21) Appl. No.: 16/606,504

(22) PCT Filed: Apr. 20, 2018

(86) PCT No.: PCT/CA2018/050473
§ 371 (c)(1),
(2) Date: Oct. 18, 2019

(87) PCT Pub. No.: WO2018/191824
PCT Pub. Date: Oct. 25, 2018

(65) Prior Publication Data
US 2020/0126218 A1    Apr. 23, 2020

Related U.S. Application Data

(60) Provisional application No. 62/487,848, filed on Apr. 20, 2017.

(51) Int. Cl.
*G06T 7/00* (2017.01)
*G16H 20/40* (2018.01)
(Continued)

(52) U.S. Cl.
CPC .......... *G06T 7/0012* (2013.01); *G06K 9/6267* (2013.01); *G16H 20/10* (2018.01);
(Continued)

(58) Field of Classification Search
CPC ................ G06T 7/0012; G06T 7/0014; G06T 2207/10072; G06T 2207/10088;
(Continued)

(56) References Cited

U.S. PATENT DOCUMENTS 7,783,094 B2 * 8/2010 Collins ................. G06T 7/0012
382/128
2006/0147101 A1 * 7/2006 Zhang ....................... G06T 5/30
382/131

(Continued)

OTHER PUBLICATIONS

Extended European Search Report for EP Application No. 18787169.4, dated Dec. 10, 2020.
(Continued)

*Primary Examiner* — Nay A Maung
*Assistant Examiner* — Jose M Torres
(74) *Attorney, Agent, or Firm* — Dorsey & Whitney LLP (57) ABSTRACT

Systems and methods for determining a disease state of image elements are disclosed herein. An example method may include providing quantitative and non-quantitative images, determining a correspondence map of the quantitative images to an atlas, and determining candidate elements of the quantitative images by comparing the elements of the quantitative images to atlas elements of the atlas. The example method may also include localizing the candidate elements in the non-quantitative images, classifying the candidate elements based on properties of the non-quantitative images, and determining a disease state of the candidate elements.

29 Claims, 7 Drawing Sheets

(51) Int. Cl.
*G16H 50/70* (2018.01)
*G16H 50/20* (2018.01)
*G16H 20/10* (2018.01)
*G06K 9/62* (2022.01)

(52) U.S. Cl.
CPC .............. *G16H 20/40* (2018.01); *G16H 50/20* (2018.01); *G16H 50/70* (2018.01); *G06T 2207/10088* (2013.01)

(58) Field of Classification Search
CPC ........... G06T 2207/10116; G06T 2207/20021; G16H 20/10; G16H 20/40; G16H 30/40; G16H 50/20; G16H 50/70; G06K 9/6267; A61B 5/055; A61B 5/7264; A61B 6/032; A61B 6/037; A61B 6/5211; A61B 2576/00; G06V 10/764; G06V 30/19173
See application file for complete search history.

(56) References Cited

U.S. PATENT DOCUMENTS

| | | | |
|---|---|---|---|
| 2007/0019846 | A1 | 1/2007 | Bullitt et al. |
| 2007/0081712 | A1* | 4/2007 | Huang ..................... G06T 7/38 382/128 |
| 2007/0133852 | A1* | 6/2007 | Collins ................ A61B 6/5247 382/128 |
| 2008/0118125 | A1 | 5/2008 | Mahesh et al. |
| 2010/0080434 | A1* | 4/2010 | Seifert ...................... G06T 7/11 382/131 |
| 2010/0128953 | A1* | 5/2010 | Ostrovsky-Berman ..................... G06T 7/344 382/131 |
| 2012/0068699 | A1 | 3/2012 | Horkay et al. |
| 2013/0044927 | A1* | 2/2013 | Poole ................... G06T 7/0014 382/131 |
| 2015/0313882 | A1* | 11/2015 | Beller .................... A61K 45/06 546/113 |
| 2016/0203263 | A1* | 7/2016 | Maier .................... G16H 30/40 705/2 |
| 2016/0300343 | A1* | 10/2016 | Gazit ................... A61B 6/5211 |

OTHER PUBLICATIONS

International Search Report and Written Opinion dated Jun. 1, 2018 for PCT Application No. PCT/CA2018/050473, 9 pages.

* cited by examiner

IDENTIFICATION OF CANDIDATE ELEMENTS IN IMAGES FOR DETERMINATION OF DISEASE STATE USING ATLAS ELEMENTS

CROSS-REFERENCE TO RELATED APPLICATION(S)

This application is a 35 U.S.C. § 371 National Stage Application of PCT Application No PCT/CA2018/050473, filed Apr. 20, 2018, which claims the benefit under 35 U.S.C. § 119 of the earlier filing date of U.S. Provisional Application Ser. No. 62/487,848 filed Apr. 20, 2017, the entire contents of which are hereby incorporated by reference, in their entirety, for any purposes.

TECHNICAL FIELD

Examples described herein relate to a method of determining a disease state of tissue with quantitative images and a system for performing same.

BACKGROUND

Medical images are comprised of intensity values at various points in space which are typically arranged in a regular cartesian grid. The grid may for example be two-dimensional, such as for planar x-ray imaging or MR slice imaging; three-dimensional, such as for 3D CT or 3D MRI imaging, or four dimensional, such as for respiratory-correlated 4D CT imaging. Intensity values depend on the imaging modality being used; for example, they may correspond to x-ray attenuation, or be related to a concentration of water molecules. Intensity values are often relative, e.g., their values do not have any meaning on their own but only in providing contrast between neighboring points in the grid. Clinicians may, for example, use the variations in contrast to visually distinguish between cancerous and non-cancerous tissues.

In quantitative medical imaging, acquisition and reconstruction techniques attempt to produce images whose intensity values are absolute, e.g., their intensity values are related to a physical or functional property of the patient at that point. A potential advantage of quantitative imaging is that they could be used to diagnose areas of malignancy within the patient based on intensity values themselves, rather than subjectively comparing variations in intensity across the images. In practice, quantitative medical imaging is confounded by large uncertainties in the relationship between intensity values and patient properties.

Visually searching through large medical imaging datasets and interpreting intensity values in light of these variations is both time consuming and requires a high degree of experience, particularly for whole body imaging where there is no known limited region of suspected disease. Methods to automate diagnosis are confounded by the uncertainties in intensity values. The present disclosure is aimed at meeting such a need.

SUMMARY

Example methods and systems for determining candidate elements and/or disease states of same are disclosed herein. An example method may include providing at least one quantitative image of a subject, each of the at least one quantitative images including elements, providing an atlas corresponding to the subject, the atlas including atlas elements, each of the atlas elements comprising a metric distribution, determining a correspondence map relating elements of the at least one quantitative image to corresponding atlas elements, and determining candidate elements by comparing a value of certain elements of the at least one quantitative image with the metric distribution of related atlas elements of the correspondence map.

The example method may also include providing at least one additional image of the subject, each of the at least one additional images including elements, localizing the candidate elements to corresponding elements of the at least one additional image, classifying the candidate elements into at least one class based on properties of the corresponding elements of the at least one additional image, and determining a disease state of the candidate elements by analyzing the at least one class of the at least one additional image corresponding to the candidate elements.

An example method may include localizing candidate elements of a quantitative image to corresponding elements of at least one additional image, classifying the candidate elements into at least one class based on properties of the corresponding elements of the at least one additional image, and determining a disease state of the candidate elements by analyzing the at least one class of the at least one additional image corresponding to the candidate elements.

An example system may include at least one processing unit and at least one computer readable media encoded with instructions which, when executed cause the system to: provide at least one quantitative image and at least one additional image of a subject, each of the at least one quantitative image and the at least one additional image including elements; provide an atlas corresponding to the subject, the atlas including atlas elements, each of the atlas elements including a metric distribution; determine a correspondence map relating elements of the at least one quantitative image to corresponding atlas elements; determine candidate elements by comparing a value of certain elements of the at least one quantitative image with the metric distribution of related atlas elements of the correspondence map; localize the candidate elements to corresponding elements of the at least one additional image; classify the candidate elements into at least one class based on properties of the corresponding elements of the at least one additional image; and determine a disease state of the candidate elements by analyzing the at least one class of the at least one additional image corresponding to the candidate elements.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

all arranged in accordance with at least some embodiments of the present disclosure.

DETAILED DESCRIPTION

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are implicitly contemplated herein.

This disclosure is drawn, inter alia, to methods, systems, products, devices, and/or apparatuses generally related to providing at least one quantitative image of a subject, each of the at least one quantitative images including elements. An atlas corresponding to the subject may be provided. The atlas includes atlas elements, each of the atlas elements including a metric distribution. A correspondence map relating elements of the at least one quantitative image to corresponding atlas elements may be determined. Candidate elements may be determined by comparing a value of certain elements of the at least one quantitative image with the metric distribution of related atlas elements of the correspondence map. The disclosure may also involve providing at least one additional image of the subject, each of the at least one additional images including elements. The candidate elements may be localized to corresponding of the elements of the at least one additional image. The candidate elements may be classified into at least one class based on properties of the corresponding elements of the at least one additional image. A disease state of the candidate elements may be determined by analyzing the at least one class of the at least one additional image corresponding to the candidate elements.

Figure 1:
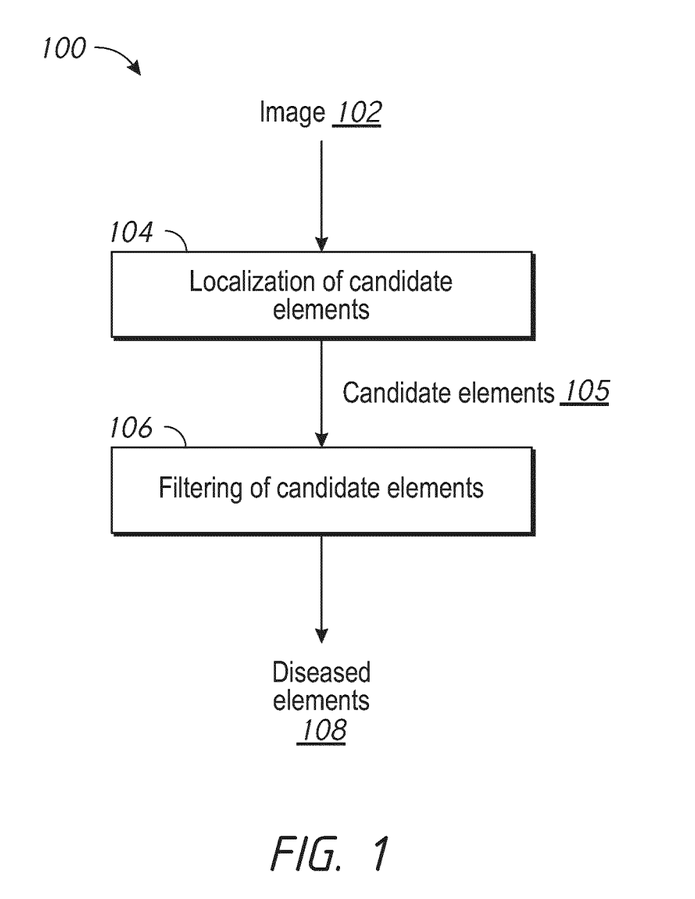
FIG. 1 is a flow chart of a method for determining a disease state of tissue arranged in accordance with an embodiment of the present disclosure.

FIG. 1 is a flow chart of a method for determining a disease state of tissue arranged in accordance with an embodiment of the present disclosure. An example method may include one or more operations, functions or actions as illustrated by one or more of blocks 100, 102, 104, 105, 106, and/or 108. The operations described in the blocks 100 through 108 may be performed in response to execution (such as by one or more processors described herein) of computer-executable instructions stored in a computer-readable medium, such as a computer-readable medium of a computing device or some other controller similarly configured.

The method 100 includes at least one image 102. Block 104 depicts "Localization of candidate elements" and may accept the at least one image 102 as an input. Block 104 may output candidate elements 105. Block 104 may be followed by block 106, which may accept the candidate elements 105 as inputs and which depicts "Filtering of candidate elements". Block 106 may output a diseased element 108 of tissue.

The one or more images 102 may be medical images of a subject. Images 102 may be acquired during method 100, or may have been previously acquired. If previously acquired, the images 102 may be stored on storage media, such as computer readable media until ready for use in method 100. The images 102 may have been acquired at the same location the method 100 is being performed, or may have been transmitted from a remote location. The images 102 may be transmitted via a wired or wireless connection to location the method 100 is being performed. Images 102 may be a single image or a plurality of images, which may include a mix of different imaging modalities. In certain embodiments the modalities may include magnetic resonance imaging (MRI), ultrasound, optical imaging, x-ray, computed tomography (CT), positron emission tomography (PET), or combinations thereof. The images 102 may be quantitative images, non-quantitative images, or a combination. The at least one image 102 may include elements such as pixels, voxels, groups of voxels corresponding to an anatomical structure, surfaces, or combinations thereof.

Block 104 recites "Localization of candidate elements". The at least one image 102 is analyzed for abnormal regions. Properties of each of the elements (or groups of elements) of the image 102 are determined and analyzed. The elements may be components of the image, and may be raw image data (e.g., intensity values for each pixel), may be processed image data (e.g., a normalized or background corrected intensity values for each pixel), may be groupings of image components into identified features (e.g., coordinates of a centroid of pixels identified as a tissue structure), or may be combinations thereof. Multiple different types of elements may exist in images 102. Different properties and values may be associated with different types of elements (e.g., location, intensity, texture, type of tissue, etc.). In some examples the elements may be pixels, voxels, groups of voxels that have been identified as anatomical structures, surfaces that have been extracted from the data via a segmentation algorithm, annotations, points in image coordinate space, or combinations. Other elements maybe used in other examples. The elements may be compared to a normal range or probability distributions of corresponding to different tissues. Elements determined to be of interest are output as candidate elements 105. The candidate elements 105 may represent a subset of the elements of the image 102. The candidate elements 105 may be regions with abnormal tissue properties and may be regions of interest for further clinical investigation. The candidate elements 105 may be used on their own, for example, to guide medical treatment of a subject. The method 100 may continue with block 106 which filters the candidate elements 105.

Block 106 recites "Filtering of candidate elements". Block 106 may accept the candidate elements 105 as an input. Block 106 may use additional properties of the at least one image 102 to determine which (if any) of the candidate elements 105 represent diseased tissue. Block 106 may use the same or different information from the at least one image 102 as block 104. Block 104 and Block 106 may use different images which correspond to the same patient. Block 106 may output a set of diseased elements 108, which represent a subset of the candidate elements 105. The diseased elements 108 may represent areas of the images which correspond to diseased tissue of the subject.

Although the method 100 shows blocks 104 and 106 functioning together, it is to be understood that each could be used independently. For example, a clinician could determine candidate regions of interest through some other method and then use those as an input to block 106 for filtering. Similarly, a clinician could analyze a set of images with block 104 and then use the produced candidate elements 105 without proceeding to block 106.

The method 100 may involve feedback from an operator (e.g., a doctor or technician) or may operate automatically in a user-independent fashion. The candidate elements 105 may be presented to the operator for review. The operator may be asked to accept the located candidate elements 105 or edit them before block 106. The method 100 may display the candidate elements 105 and/or the diseased elements 108 as results to an operator. The operator may review, validate, and/or edit the results. The operator may manage patient health based on the results. As an example, further tests may be ordered based on the candidate elements 105, or treatment managed based on the status of the diseased elements 108. The method 100 may be used to automatically manage patient health by using the candidate elements 105 and/or disease elements 108 with an automated health management system, such as a dosage calculator. Accordingly, identification of one or more diseased elements may result in a diagnosis—e.g., cancer, inflammation, tumor. Responsive to the diagnosis, various pharmaceuticals may be administered to the patient, and/or treatments preformed (e.g., biopsy, chemotherapy, dialysis, etc.).

Figure 2:
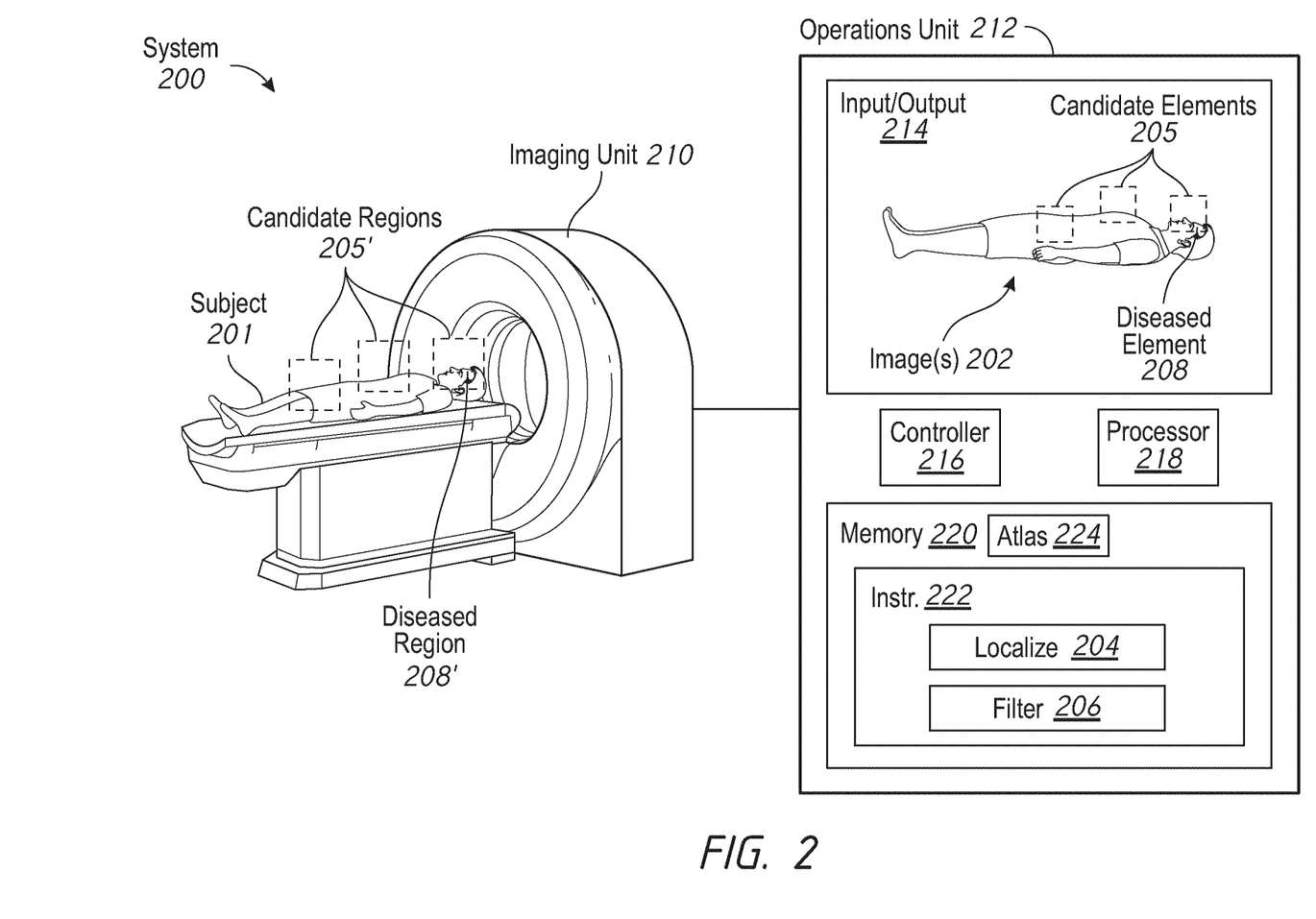
FIG. 2 is a schematic diagram depicting a system for determining a disease state of tissue arranged in accordance with an embodiment of the present disclosure.

FIG. 2 is a schematic diagram depicting a system for determining a disease state of tissue. The system 200 may be used to perform a method of determining a disease state of tissue, such as method 100 of FIG. 1. The system 200 includes a subject (e.g., a patient) 201, candidate locations (or regions) 205', disease locations (or regions) 208', imaging unit 212, and operations unit 210. The operations unit 212 may include an input/output unit (e.g., a display) 214, a controller 216, a processor 218, and a memory 220. The imaging unit 212 may produce an image 202 which may be sent to the operations unit 212 to be stored in memory 220 and/or displayed on input/output unit 214. The image 202 includes candidate elements 205 and disease elements 208. The memory 220 may include instructions 222, including instructions to localize a candidate element 204 and filter the candidate elements 206, and an atlas 224.

The subject 201 may include candidate regions 205' and/or disease locations 208' within their body. The imaging unit 210 may scan or image all or part of the subject 201 to produce data which is sent to operations unit 212 to form an image 202. The operations unit 212 may include an input/output unit 214, a controller 216, a processor 218, and memory 220. The memory stores instructions 222 which may be accessed to cause the processor 218 to perform certain operations. The processor 218 and/or memory may receive data from the imaging unit 210 to produce image 202. The processor 218 may execute instructions 222 of the memory such as localizing candidate elements 204 and/or filtering candidate elements 206 to produce candidate elements 205 and disease elements 208 of the image 202. The candidate elements 205 of the image 202 may correspond to the candidate locations 205' of the subject 201, and the disease elements 208 of the image 202 may correspond to the disease locations 208' of the subject 201. The atlas 224 may be accessed by the processor 218 while executing one or more the instructions 222.

The subject 201 may be a mammal such as a human. The subject 201 may be a patient who is exhibiting symptoms or is undergoing treatment and/or monitoring for a disease or condition. The subject 201 may be a member of the general population or otherwise asymptomatic. The subject 201 may have one or more candidate locations 205' and/or one or more diseased region 208'. The regions 205',208' may be on an external surface of the subject 201 (e.g., on the skin) or may be located internally. The one or more diseased regions 208' may be a subset of the one or more candidate locations 205'. The candidate locations 205' may be areas of tissue which have properties which fall outside, or have a sufficient probability of falling outside, a normal clinical range for that tissue. They may also be detected using an artificial intelligence algorithm. The one or more diseased regions 208' may be locations containing structures which are harmful to the subject 201 or which may become harmful to the subject 201 in the future. In one example, the diseased region 208' may be a region of cancerous cells, such as a tumor. Other diseased tissues or conditions may be investigated in other examples.

The imaging unit 210 may produce one or more images (such as images 202) of the subject 201. The imaging unit may produce a single image or a plurality of images of the subject 201. The imaging unit 210 may produce images of all or a portion of the subject 201. The imaging unit 210 may include multiple imaging modalities such as MRI, ultrasound, optical imaging, x-ray, CT, PET, or combinations thereof. In some cases the multiple imaging modalities may physically be installed in different locations, and the patient transported to the different locations for separate imaging sessions. The imaging unit 210 may produce a whole body scan of the subject 201. The imaging unit may produce quantitative images, non-quantitative images, or combinations. The imaging unit 210 may be coupled to the operations unit 212 by wired and/or wireless communication. The imaging unit 210 may send raw data to the operations unit 212 or may send processed data to the operations unit 212. The imaging unit 210 and the operations 212 may be located remotely from each other. The data may be stored on a non-transitory medium, such as a computer readable medium by the imaging unit 210, and retrieved by the operations unit 212 at a later time.

The images 202 produced by the imaging unit 210 may be used as images 102 of FIG. 1. The images 202 may be stored, displayed, and/or analyzed by the operations unit 212. The images 202 may be representative of the subject 201. The images may include elements such as pixels, voxels, groups of voxels corresponding to an anatomical structure, surfaces, or combinations thereof. The images 202 may include quantitative images, where a value (e.g., an intensity) of each element of the image 202 has an absolute value which relates to a property of the subject 201 at a location corresponding to the element. The images may undergo image processing by the processor 218 and/or by the imaging unit 210. The image processing may include correcting for distortions or artifacts, normalization of values, or combinations. The values of the elements of the images 202 may be normalized so that they are, for example, between 0 to 255. Other ranges may be used in other examples. The imaging unit 210 may be calibrated. The calibration may involve using the imaging unit 210 to produce an image of a tissue phantom (not shown) with known properties.

The operations unit 212 receives data from the imaging unit 210. The operations unit 212 may be a computer. The operations unit 212 uses data from the imaging unit 210 to produce the images 202. The data may be saved into memory 220. Controller 216 may cause the processor 218 to render the images 202 onto an input/output 214. In some examples, the input/output 214 may be a display, such as a computer monitor. The controller 216 may also send instructions to imaging unit 210 to control aspects of the imaging of the subject 201. The controller 216 may cause the processor 218 to execute instructions 222 stored in the memory.

The instructions 222 in memory 220 may be used to analyze the images 202. The instructions 222 may include instructions to localize candidate elements 204 (such as block 104 of FIG. 1). The instructions 222 may include instructions to filter candidate elements 206 (such as block 106 of FIG. 1). The instructions 204, 206 may be run sequentially on the same images 202 or may be run as separate steps. The instructions 204, 206 may produce candidate elements 205 and/or diseased elements 208 of the images 202. The input/output 202 may display the images 202 along with one or more of the candidate elements 205 and diseased elements 208. The memory 220 may store additional information such as atlas 224, which may be used in one or more of the instructions 222.

Figure 3:
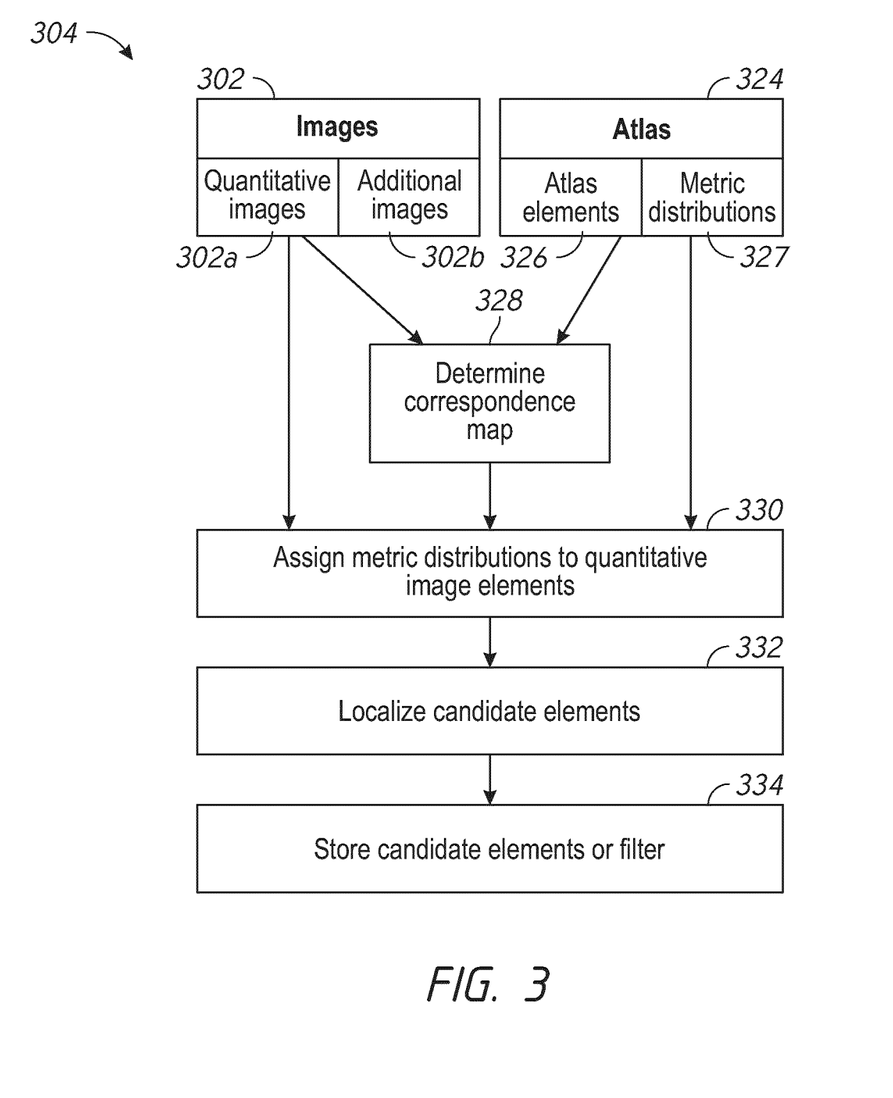
FIG. 3 is a flow chart of a method of localizing candidate elements arranged in accordance with an embodiment of the present disclosure.

FIG. 3 is a flow chart of a method 304 of localizing candidate elements arranged in accordance with an embodiment of the present disclosure. An example method may include one or more operations, functions or actions as illustrated by one or more of blocks 302, 302a, 302b, 324, 326, 327, 328, 330, 332, and/or 334. The operations described in the blocks 302 to 334 may be performed in response to execution (such as by one or more processors described herein) of computer-executable instructions stored in a computer-readable medium, such as a computer-readable medium of a computing device or some other controller similarly configured.

The method 304 includes at least one image 302 including quantitative images 302a. The images 302 may also include additional images 302b, which may be quantitative images, non-quantitative images or a combination. The method also includes atlas 324 which includes atlas elements 326 and metric distributions 327. An example process may begin with block 328, which recites "Determine correspondence map" and accepts the images 302 and the atlas 324 as inputs. Block 328 may be followed by block 330 which recites "Assign metric distributions to quantitative image elements." Block 330 may be followed by block 332, which recites "Localize candidate elements". Block 332 may be followed by block 334, which recites "Store candidate elements or filter".

The method 304 may be a detailed method of localizing candidate elements, such as methods 104 and 204 of FIG. 1-2. The images 302 may be similar to, or may be the same as, images 102 of FIG. 1 and images 202 of FIG. 2. The images 302 may include a mix of quantitative images 302a and additional images 302b. The quantitative images 302a and additional images 302b are each composed of elements as described herein. The quantitative images 302a have elements with values which are absolute, e.g., their values are related to a physical or functional property at that point of the image. The quantitative images 302a may be calibrated. The quantitative images 302a may include quantitative MRI, quantitative PET, quantitative ultrasound, or combinations. Examples of quantitative images include a whole body diffusion weighted imaging MM (DWI MM). Examples of non-quantitative images include short-TI inversion recovery (STIR) MM, T1-weighted MRI images, T2-weighted MRI images, CT, PET, single-photon emission computed tomography (SPECT), ultrasound, or combinations.

The atlas 324 is a representation of average values from a normal patient population. The atlas 324 may be constructed from one or more previously acquired images from a normal patient population, may be artificially generated from statistics or generalizations about a normal patient population, or combinations. The atlas 324 may include a single composite image of an average or representative patient, or a number of such images. The atlas 324 may represent all normal patients, or may represent a subset of the normal patient population. The subset may be restricted by, for example, one or more of gender, age, weight, height, body shape, or other factors. The atlas 324 may be chosen or filtered to correspond to a subject of the images 302 (such as subject 201 of FIG. 2). In an example, if the subject is a 15 year old woman, the atlas might be filtered by 'female' and 'teenager' and an atlas may be produced which averages only patient scans of female teenagers. Other filters may be used in other examples.

The atlas 324 may include atlas elements 326 and metric distributions 327. The atlas elements 326 may each be associated with one or more of the metric distributions 327. The atlas elements 326 may be image pixels, image voxels, segmented surfaces, reference points, reference structures, or combinations. The metric distributions 327 may be a range of 'normal' values for each atlas element 326. The metric distribution 327 may include intensity values or values calculated from intensity values, such as average intensity or texture value. In one embodiment where the quantitative images 202a are DWI MRI images, the metric distributions 327 are a range of expected diffusion values for each atlas element 326. Other quantitative images and metric distributions may be used in other examples. The metric distributions 327 may be normalized values. The metric distributions 327 may be a range of probability density distribution of intensity values, an average and standard deviation of intensity values, a range of expected texture values, or combinations. The atlas 324 may include multiple images each including atlas elements with metric distributions.

Block 328 describes "Determine Correspondence Map" and accepts inputs including the quantitative images 302a and atlas 324. During block 328, each element of the quantitative images 302a is matched with one or more of the atlas elements 326. The atlas elements 326 may be mapped onto elements of the quantitative image 302a, or the elements of the quantitative image 302a may be mapped onto the atlas elements 326. The mapping may adjust for differences between the size and shape of the normal patient(s) in the atlas 324 and the size and shape of the subject of the quantitative images 302a. In one embodiment, the correspondence mapping may be performed by using a deformable registration algorithm. In another embodiment, the quantitative image 302a may be segmented to separate it into one or more structure elements, and the atlas elements 326 may be defined as structure elements. The quantitative image 302a elements may be matched to the atlas elements 326 by comparing size, morphology, and/or positioning of the elements. For example, lymph node chains may have sizes of about 2 cm in the neck and 1 cm in the chest, which can be combined with morphological information to identify corresponding structures in the images. Other methods of determining the correspondence map, such as using artificial intelligence algorithms, may be used in other examples.

Figure 4:
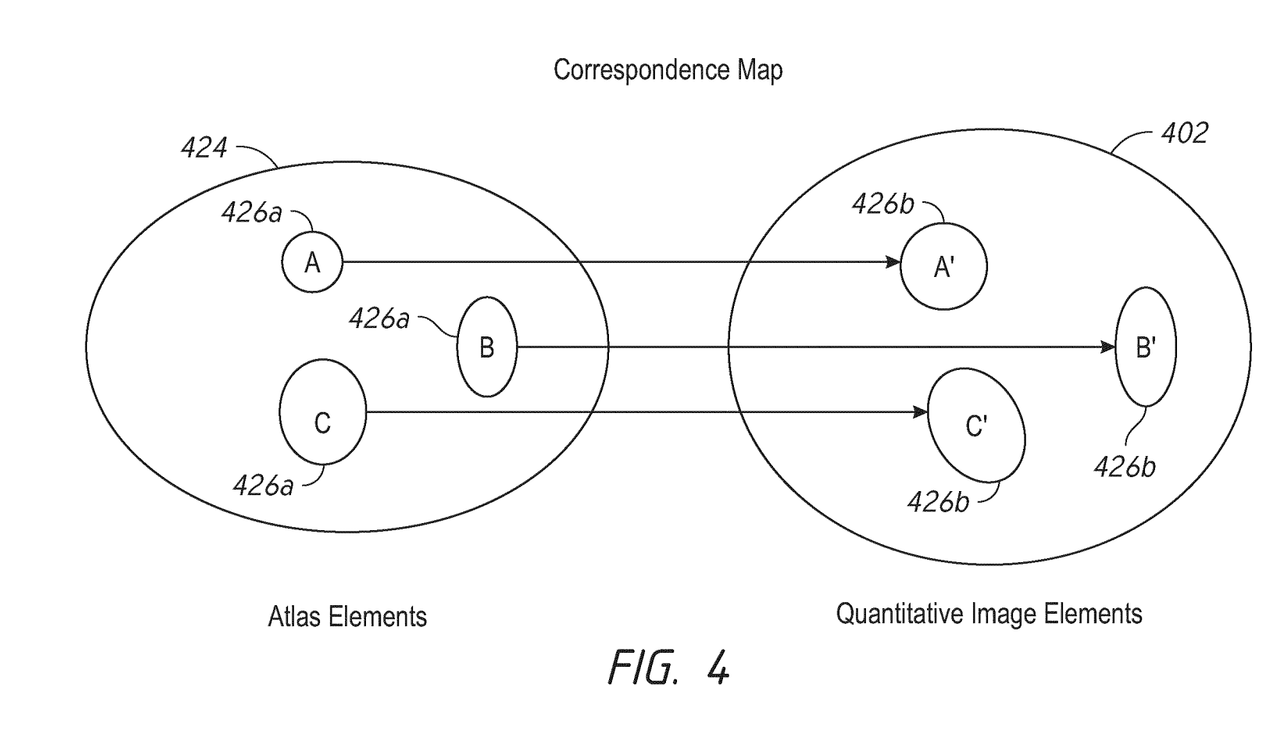
FIG. 4 is a schematic diagram of a correspondence map arranged in accordance with an embodiment of the present disclosure.

FIG. 4 is a schematic diagram of a correspondence map which may be used as the correspondence map of block 328 of FIG. 3. FIG. 4 includes an atlas 424 with atlas elements 426a and an image 402 with mapped atlas elements 426b. In the example of FIG. 4, the atlas elements 426a represent structures which are being mapped onto corresponding elements of the image 402. As shown by the arrows, the atlas elements 426a undergo a change in size and shape as they are mapped onto image 402 to become mapped elements 426b. Each set of corresponding elements 426a,b may have a metric distribution corresponding to the structure, type of tissue, or other features that are shared by the set.

Referring back to FIG. 3, after determining a correspondence map, the method 304 continues with block 332 which recites "Localize candidate elements". The elements of the quantitative image 302a are compared with the metric distributions 327 of the corresponding atlas elements 326 determined by the correspondence map. The comparing may involve a direct comparison such as comparing values to a threshold, or may involve machine learning, deep learning, or other artificial intelligence algorithm. In some embodiments, a user (e.g., a clinician) may provide input to the system in order to localize the candidate elements.

Figure 5:
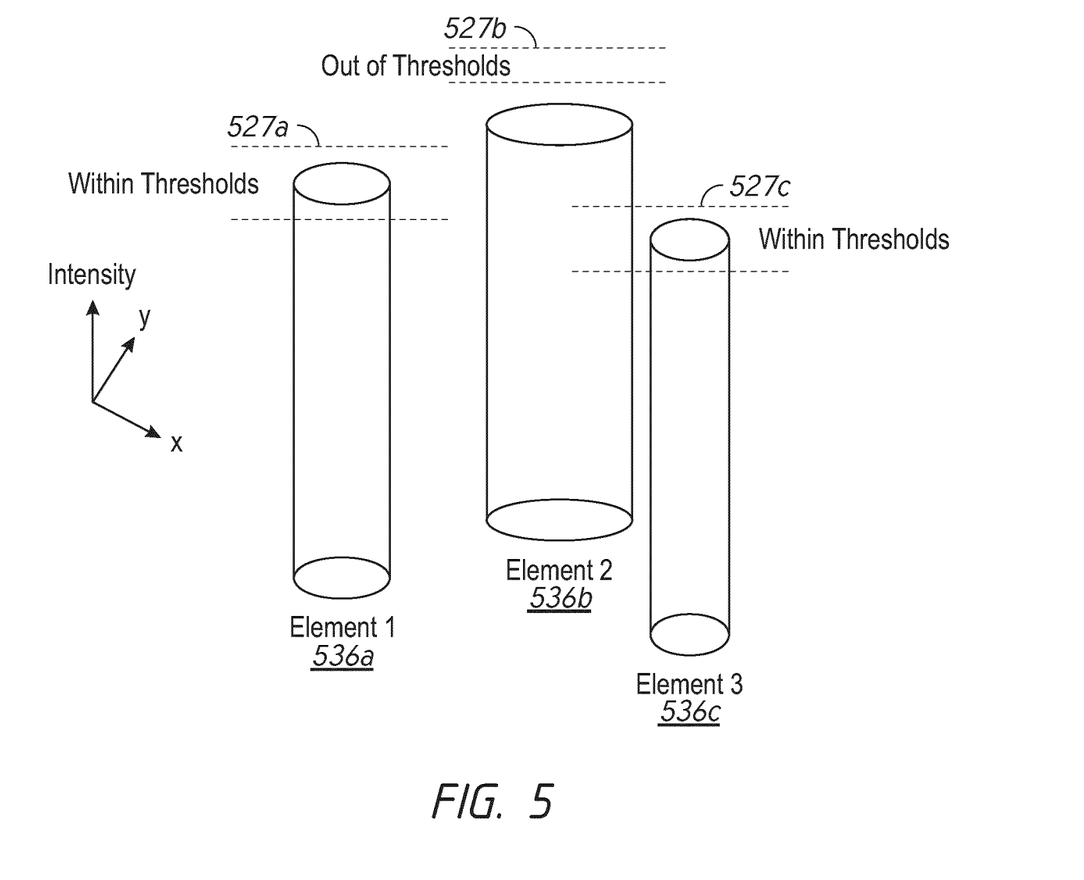
FIG. 5 is a schematic diagram of metric distributions arranged in accordance with an embodiment of the present disclosure.

FIG. 5 depicts a schematic diagram of metric distributions which may be an example of the localizing candidate elements of block 332 of FIG. 3. FIG. 5 includes elements 536a-c which may be elements of a quantitative image, and ranges 527a-c which may be metric distributions of an atlas. In this example, comparison of the values of the elements of the quantitative images and the metric distributions of the corresponding of the atlas elements is done by determining if the value of the quantitative image element falls within the range of values of the metric distribution. FIG. 5 depicts three elements 536a-c, each of which is associated with a separate range of values 527a-c. Elements 536a and 536c have values which fall within the ranges 527a and 527c respectively, and would be considered normal (e.g., not a candidate element). Element 536b falls outside the range 527b, and would not be considered normal. Element 536b may be reported as a candidate element (e.g., candidate element 105 of FIG. 1). Other methods of comparing the metric distributions to the values of the quantitative images may be used in other examples.

Referring back to FIG. 3, the method 304 involves block 334, which recites "Store candidate elements or filter". The localized candidate elements may be stored on a memory (such as memory 220 of FIG. 2) and/or undergo further analysis, such as filtering. The candidate elements may undergo additional processing. The coordinates or a centroid of the candidate elements may be identified. The candidate elements may be grouped together into unified elements. A system (such as system 200 of FIG. 2) may display the localized candidate elements. The candidate elements 305 may be displayed as an overlay on the images 302.

Figure 6:
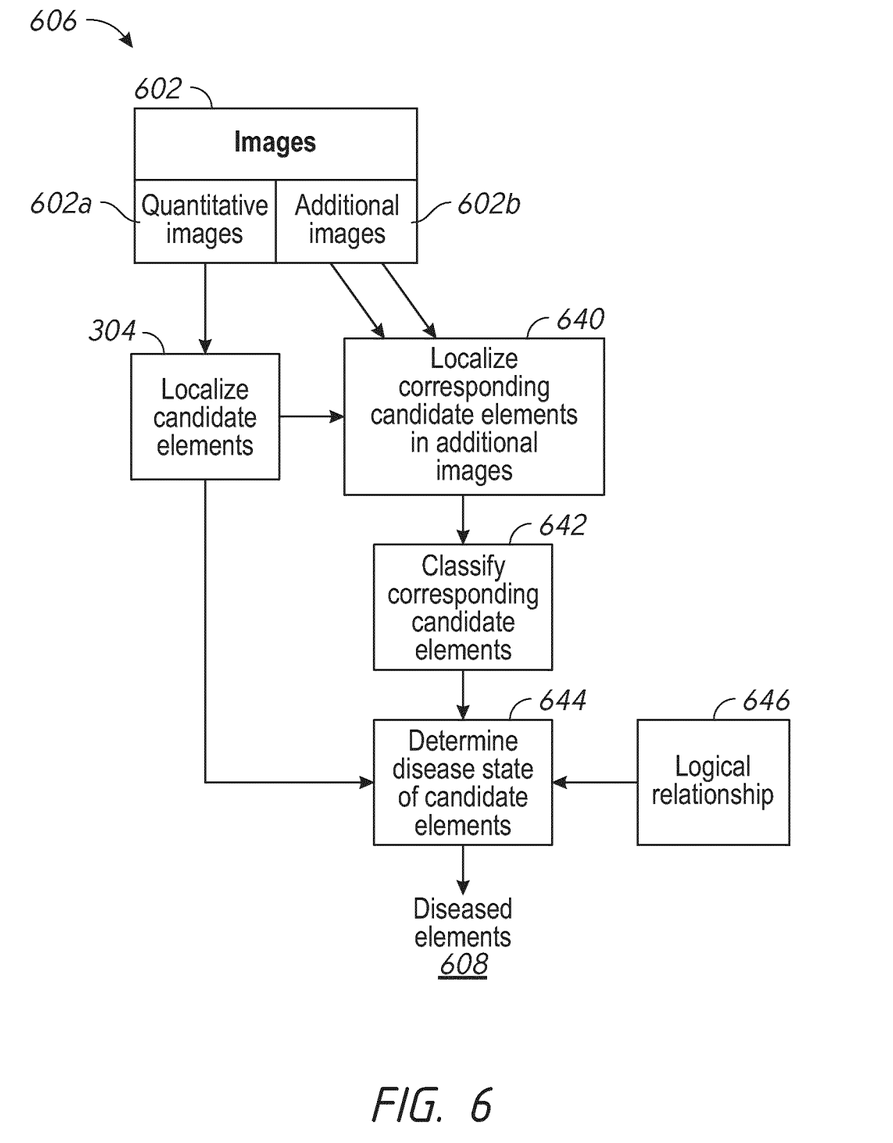
FIG. 6 is a flow chart of a method of filtering candidate elements arranged in accordance with an embodiment of the present disclosure.

FIG. 6 is a flow chart of a method 606 of filtering candidate elements arranged in accordance with an embodiment of the present disclosure. An example method may include one or more operations, functions or actions as illustrated by one or more of blocks 602, 602a, 602b, 304, 640, 642, 644, 646, 608. The operations described in the blocks 602 to 646 may be performed in response to execution (such as by one or more processors described herein) of computer-executable instructions stored in a computer-readable medium, such as a computer-readable medium of a computing device or some other controller similarly configured.

The method 606 includes at least one image 602 including quantitative images 602a and additional images 602b. An example process may begin with block 640, which recites "Localize corresponding candidate elements in additional images" and accepts the additional images 602b, and the results of block 304 "localize candidate elements" as input. Block 640 may be followed by block 642 which recites "Classify corresponding candidate elements." Block 642 may be followed by block 644, which recites "Determine disease state of candidate elements". Block 644 accepts as an input block 646, which recites "Logical relationship". Block 644 may output diseased elements 608.

The method 606 may be used as the filtering of candidate elements 105, 205 of FIGS. 1 and 2 respectively. The method 606 may be a continuation of method 304, or may be a stand-alone method. Similarly the images 602 including quantitative images 602a, and additional images 602b may be the images 102, 202, 302, 302a, 302b of FIGS. 1-3 respectively. Block 304 is shown reciting "Localize candidate elements", and may represent the method 304 of FIG. 3, which results in a set of candidate elements. The method 606 may also be used on its own with new images 602 and a set of candidate elements determined by a different process, such as identification by a clinician.

Block 640 recites "Localize corresponding candidate elements in additional images". During this step, candidate elements identified in quantitative images 602a (such as by block 304) are located in corresponding additional images 602b. The additional images 602b may be quantitative or non-quantitative images. The additional images 602b may be made up of elements similar to the elements of quantitative images 602a. The candidate elements may be individual elements or groups of elements which were previously identified for further review. In one example, coordinates of the candidate elements may be matched to coordinates of elements in the additional images 602b. In another example, a non-rigid registration algorithm may be used to register quantitative images 602a to the additional images 602b. In yet another example, common elements of the images 602a,b may be identified by segmenting structures in each image. Other methods of localization may be used in other examples.

Block 642 recites "Classify corresponding candidate elements". Properties of the additional images 602b corresponding to the candidate elements may be assigned to different classes. Classes may be binary, such as 'dark' and 'bright', or 'hard' and 'soft'. Classes may also involve more than two elements such as 'dark', 'bright', and 'undetermined' or a number of discrete values assigned (e.g., brightness on a scale from 1-10). The class of a given candidate element may be determined by comparing average, standard deviations, or texture values within a candidate element to average surrounding values. The comparing may be to determine if the value within the candidate element is higher or lower than an average of surrounding elements. In some examples, a machine learning algorithm may be used to assign classes to the candidate elements.

Block 644 recites "Determine disease state of candidate elements". Based on the classes applied to the candidate elements, they may be assigned a status of diseased or not diseased. Other statuses, such as, for example, a type of disease may also be determined. A logical relationship 646 may be applied to the classes of the candidate elements from the non-quantitative images 602b. The logical relationship 646 may be specific to the types of images 602 and/or the application. The logical relationship 646 may reflect a logical understanding of what circumstances might have caused an element of the quantitative images 602a to be identified as a candidate element. The logical relationship 646 may compare classes of the additional images 602b, values of the quantitative images 602a, or both. The logical relationships 646 may be altered to reflect different image types, user preference, updated scientific knowledge, or other factors.

An example of a logical relationship is expressed in Table 1. In this example there is a single quantitative image (DWI) and two additional non-quantitative images (STIR and T1). Candidate elements were previously located by examining the DWI image for elements with abnormal water movement. For the purposes of this example, abnormal water movement may be considered to be caused by the presence of fluid or a cyst, by blood (such as in fat or bone-marrow), or by a tumor. STIR images are bright when a fluid or cyst is present, but dark when a tumor is present. T1 images are bright when fat/bone-marrow are present, but dark when a tumor is present. The columns of Table 1 show the possible imaging modalities. The rows of Table 1 show a diagnosis based on the results of each of the 3 imaging modalities. In Table 1 an 'X' signifies that the classification of that column is unimportant to the diagnosis, and may not need to be considered. Thus, a tumor is diagnosed when a given candidate element is dark in both STIR and T1. Fluid and/or a cyst is identified when a candidate element is bright in the STIR image, and blood is identified when the T1 image is bright. Other logical relationships may be established for other examples.

TABLE 1

Logical Relationship

| Diagnosis | DWI | STIR | T1 |
|---|---|---|---|
| Tumor | Candidate | Dark | Dark |
| Fluid/Cyst | Candidate | Bright | X |
| Blood | Candidate | X | Bright |

In this manner, examples described herein may utilize quantitative images to identify candidate elements using a comparison with an atlas (e.g., average image values from a normal population). The candidate elements may then be located in other associated images (e.g., non-quantitative images). A binary classification (e.g., bright/dark) may be used to evaluate the candidate elements in the non-quantitative images to arrive at an identification of a diseased element.

The method 606 accordingly outputs diseased elements 608. The diseased elements 608 are elements of the images 602 which are identified as corresponding to diseased tissue (such as disease location 208' of FIG. 2). The diseased elements 608 may reflect currently diseased tissue, or tissue which may become diseased. The method 606 may be altered (for example, by specifying logical relationships 646) to filter for other elements of interest which are not diseased tissue. The state of each candidate element may be saved, for example, on a memory (such as memory 220 of FIG. 2). A report may be generated to identify elements which are considered diseased by the method 606.

Figure 7:
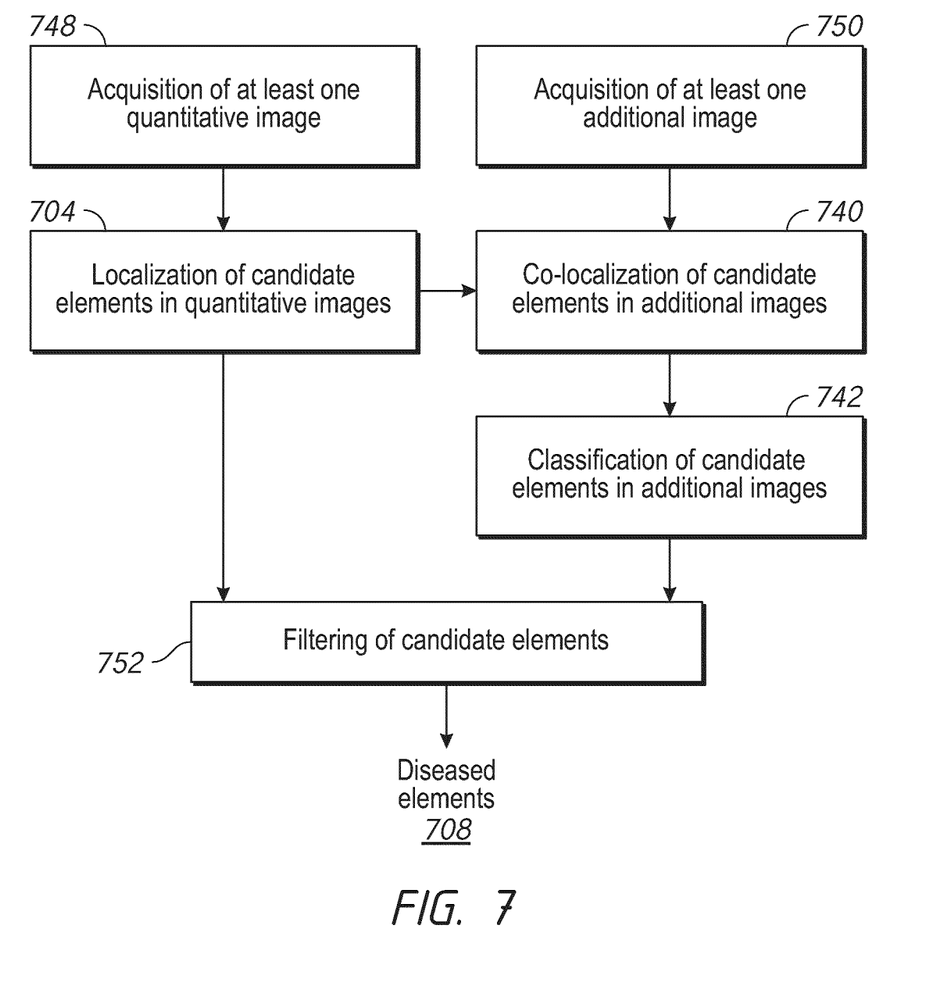
FIG. 7 is a flow chart of a method of localizing and filtering candidate elements in accordance with the present disclosure.

FIG. 7 is a flow chart of a method 700 of localizing and filtering candidate elements in accordance with the present disclosure. An example method may include one or more operations, functions or actions as illustrated by one or more of blocks 748, 750, 704, 740, 742, 752, and diseased elements 708. The operations described in the blocks 704 to 752 may be performed in response to execution (such as by one or more processors described herein) of computer-executable instructions stored in a computer-readable medium, such as a computer-readable medium of a computing device or some other controller similarly configured.

The method 700 may include block 748, which recites "Acquisition of at least one quantitative image". The method 700 may also include block 750, "Acquisition of at least one additional image". Block 704 may follow block 748 and recites "Localization of candidate elements in quant. images". Block 740 may follow block 750 and block 704 and recites "Co-localization of candidate elements in additional images." Block 742 may follow block 740 and recites "Classification of candidate elements in additional images". Block 752 may follow blocks 704 and 742 and recites "Filtering of candidate elements". Diseased elements 708 may be output from block 752.

The method 700 may be similar to other methods of determining diseased elements described herein. In method 700, the location of candidate elements and filtering to disease elements happen as part of a single process. The method 700 may be performed using a system, such as the system 200 of FIG. 2.

Blocks 748 and 750 recite "Acquisition of at least one quantitative image" and "Acquisition of at least one additional image" respectively. The images may be acquired by an imaging unit, such as imaging unit 210 of FIG. 2. The images may be previously acquired and may be stored until called up by method 700. The images may be, for example, quantitative images 202a and additional images 202b of FIG. 2. The additional images acquired in block 750 may be quantitative or non-quantitative. The images may correspond to the same subject. The images may include a plurality of different imaging modalities.

Block 704 recites "Localization of candidate elements in quant. images". As discussed herein, methods may be used to identify candidate elements of the quantitative images. These may include localizing the quantitative elements to an atlas and comparing elements of the quantitative image to atlas elements as described in method 304 of FIG. 3.

Block 740 recites "Co-localization of candidate elements in additional images". The candidate elements determined in block 704 are located in the additional images acquired in block 750. The localization may be generally similar to the localization of block 640 of FIG. 6.

Block 742 recites "Classification of candidate elements in additional images". The candidate elements of the additional images are grouped into classes based on properties of the additional images. The classification may be generally similar to the classification of block 642 of FIG. 6.

Block 752 recites "Filtering of candidate elements". In this step, the candidate elements properties in both the quantitative and additional images are compared to determine a disease state of each of the candidate elements. The value of the candidate elements in the quantitative images may be compared to one or more classes of the candidate elements in the additional images. A logical relationship may be used to determine a disease state based on the properties of the candidate elements. The output of method 700 may be a set of diseased elements 708.

The diseased elements output by one or more of FIGS. 1-7 may be used to manage a subject's health. The diseased elements may be used to diagnose a subject. For example, an estimate of survivability may be given to the subject based on the diseased elements. Follow-up tests may be ordered based on the diseased elements. For example, a biopsy of the subject may be performed in locations corresponding to the diseased elements. The diseased elements may be used (alone or with additional information) to direct and/or monitor a course of treatment. For example, drugs may be delivered to, or surgery may be performed at, a location of the subject corresponding to the diseased elements. Parameters of the treatment may be determined based on the diseased elements. For example, the dosage of a drug may be determined by the volume of diseased elements located in the images. The method may be repeated on the same subject over time to monitor a status of the diseased elements, such as monitoring disease progression.

The present disclosure is not to be limited in terms of the particular examples described in this application, which are intended as illustrations of various aspects. Many modifications and examples can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and examples are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 items refers to groups having 1, 2, or 3 items. Similarly, a group having 1-5 items refers to groups having 1, 2, 3, 4, or 5 items, and so forth.

While the foregoing detailed description has set forth various examples of the devices and/or processes via the use of block diagrams, flowcharts, and/or examples, such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the examples disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. For example, if a user determines that speed and accuracy are paramount, the user may opt for a mainly hardware and/or firmware vehicle; if flexibility is paramount, the user may opt for a mainly software implementation; or, yet again alternatively, the user may opt for some combination of hardware, software, and/or firmware.

In addition, those skilled in the art will appreciate that the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A method comprising:
   providing a quantitative image of a subject, the quantitative image being a whole body image of the subject, the quantitative image comprising elements;
   providing an atlas corresponding to the subject, the atlas comprising atlas elements, each of the atlas elements comprising a metric distribution, each of the atlas elements corresponding to an anatomical structure;
   segmenting the quantitative image into a plurality of structure elements, the structure elements being groups of the elements of the quantitative image, the structure elements each corresponding to an anatomical structure in the whole body image, wherein segmenting the quantitative image into a plurality of structure elements includes identifying each of the plurality of structure elements based on two or more of size, morphology, and location of each of the respective structure elements;
   determining a correspondence map relating the structure elements of the quantitative image to corresponding atlas elements by comparing one of size, morphology, and positioning of the structure elements of the quantitative image to the corresponding atlas elements; and
   determining candidate elements by comparing a value of certain elements of the quantitative image with the metric distribution of related atlas elements of the correspondence map.

2. The method of claim 1, further comprising:
   providing at least one additional image of the subject, each of the at least one additional images comprising elements;
   localizing the candidate elements to corresponding elements of the at least one additional image;
   classifying the candidate elements into at least one class based on properties of the corresponding elements of the at least one additional image; and
   determining a disease state of the candidate elements by analyzing the at least one class of the at least one additional image corresponding to the candidate elements.

3. The method of claim 2, wherein the at least one additional image comprises at least one additional quantitative image, at least one non-quantitative image, or combinations.

4. The method of claim 3, wherein the at least one non-quantitative image comprises a STIR image, a T1-weighted image, a T2-weighted image, a CT image, a SPECT image, a PET image, an ultrasound image, or combinations thereof.

5. The method of claim 2, further comprising acquiring at least one of the quantitative image and the at least one additional image.

6. The method of claim 2, wherein the determining the disease state comprises analyzing the value of the quantitative image.

7. The method of claim 2, further comprising image processing at least one of the quantitative image and the at least one additional image.

8. The method of claim 2, wherein the localizing the candidate elements comprises matching corresponding coordinates, using a non-rigid registration algorithm, finding common elements, an artificial intelligence algorithm, or combinations thereof.

9. The method of claim 2, wherein the classifying the candidate elements comprises comparing average, standard deviations, or texture values of one of the candidate elements to average values of elements surrounding the one of the candidate elements.

10. The method of claim 2, wherein the classifying the candidate elements comprises using an artificial intelligence algorithm.

11. The method of claim 2, wherein the at least one class comprises a binary class.

12. The method of claim 2, wherein the disease state comprises cancer.

13. The method of claim 2, wherein the determining a disease state comprises applying a logical relationship to the at least one class of the at least one additional image, the value of the quantitative image, or combinations.

14. The method claim 1, wherein the elements comprise pixels, voxels, groups of voxels corresponding to an anatomical structure, surfaces, points, annotations or combinations thereof.

15. The method of claim 1, wherein the quantitative image comprises a whole body diffusion weighted MRI image.

16. The method of claim 15, further comprising calibrating the whole body diffusion weighted MRI image using a phantom.

17. The method of claim 1, wherein the atlas comprises previously acquired quantitative data of a normal patient population.

18. The method of claim 1, wherein the atlas comprises previously acquired quantitative data of a subset of a normal patient population, the subset determined at least in part by properties of the subject.

19. The method of claim 1, wherein the atlas elements comprise image pixels, image voxels, segmented surfaces, reference points, reference structures, annotations, or combinations thereof.

20. The method of claim 1, wherein the metric distribution comprises a range of expected diffusion values, a probability density distribution of intensity values, an average and standard deviation of intensity values, a range of expected texture values or combinations for elements of the atlas.

21. The method of claim 1, wherein the determining the correspondence map comprises using a deformable registration technique.

22. A method comprising:
providing a quantitative image and at least one additional image of a subject, each of the quantitative image and the at least one additional image comprising elements:
providing an atlas corresponding to the subject, the atlas comprising atlas elements, each of the atlas elements comprising a metric distribution:
segmenting the quantitative image into a plurality of structure elements, the structure elements being groups of the elements of the quantitative image, the structure elements each corresponding to an anatomical structure in the whole body image, wherein segmenting the quantitative image into a plurality of structure elements includes identifying each of the plurality of structure elements based on two or more of size, morphology, and location of each of the respective structure elements:
determining a correspondence map relating the structure elements of the quantitative image to corresponding atlas elements of an atlas by comparing one of size, morphology, and positioning of the structure elements of the quantitative image to the corresponding atlas elements, wherein the atlas elements each correspond to a respective anatomical structure;
identifying, using the atlas, candidate elements of the whole body quantitative image of a subject by comparing a value of the structure elements of the whole body quantitative image to metric distributions of the atlas elements corresponding to the structure elements;
localizing the candidate elements of the whole body quantitative image to corresponding elements of the at least one additional image of the subject;
classifying the candidate elements into at least one class based on properties of the corresponding elements of the at least one additional image; and
determining a disease state of the candidate elements by analyzing the at least one class of the at least one additional image corresponding to the candidate elements.

23. The method of claim 22, further comprising treating a subject based on the determined disease state of the candidate elements.

24. The method of claim 23, wherein the treating the subject comprises performing a surgery, administering a drug, performing a biopsy, monitoring disease progression, or combinations.

25. A system comprising:
at least one processing unit; and
at least one computer readable media encoded with instructions which, when executed cause the system to:
provide a quantitative image and at least one additional image of a subject, each of the quantitative image and the at least one additional image comprising elements;
provide an atlas corresponding to the subject, the atlas comprising atlas elements, each of the atlas elements comprising a metric distribution;
segment the quantitative image into a plurality of structure elements, the structure elements being groups of the elements of the quantitative image, the structure elements each corresponding to an anatomical structure in the whole body image, wherein segmenting the quantitative image into a plurality of structure elements includes identifying each of the plurality of structure elements based on two or more of size, morphology, and location of each of the respective structure elements;
determine a correspondence map relating the structure elements of the quantitative image to corresponding atlas elements by comparing one of size, morphology, and positioning of the structure elements of the quantitative image to the corresponding atlas elements, each of the atlas elements corresponding to an anatomical structure;
determine candidate elements by comparing a value of the structure elements of the quantitative image with the metric distribution of related atlas elements of the correspondence map;
localize the candidate elements to corresponding elements of the at least one additional image;

classify the candidate elements into at least one class based on properties of the corresponding elements of the at least one additional image; and determine a disease state of the candidate elements by analyzing the at least one class of the at least one additional image corresponding to the candidate elements.

26. The system of claim 25, wherein the instructions further include instructions which, when executed, cause the system to apply a logical relationship to the at least one class and the values of the quantitative imaging.

27. The system of claim 25, further comprising an imaging unit configured to acquire the quantitative image and the at least one additional image.

28. The system of claim 27, wherein the imaging unit comprises an MRI.

29. The system of claim 25, further comprising an output unit configured to display the determined disease state.

* * * * *